United States Patent
Chen et al.

(10) Patent No.: US 10,492,888 B2
(45) Date of Patent: Dec. 3, 2019

(54) DENTAL MATERIALS USING THERMOSET POLYMERS

(71) Applicant: Align Technology, Inc., San Jose, CA (US)

(72) Inventors: Yan Chen, Cupertino, CA (US); Chunhua Li, Cupertino, CA (US); Srinivas Kaza, San Francisco, CA (US); Neil Brian Cramer, Boulder, CO (US); Mary Catherine Berard, Longmont, CO (US)

(73) Assignee: Align Technology, Inc., San Jose, CA (US)

( * ) Notice: Subject to any disclaimer, the term of this patent is extended or adjusted under 35 U.S.C. 154(b) by 506 days.

(21) Appl. No.: 15/201,958

(22) Filed: Jul. 5, 2016

(65) Prior Publication Data

US 2017/0007362 A1    Jan. 12, 2017

Related U.S. Application Data

(60) Provisional application No. 62/189,380, filed on Jul. 7, 2015.

(51) Int. Cl.

| | |
|---|---|
| *A61C 7/08* | (2006.01) |
| *C08F 220/18* | (2006.01) |
| *C08F 220/28* | (2006.01) |
| *C08F 222/10* | (2006.01) |
| *A61C 7/12* | (2006.01) |

(Continued)

(52) U.S. Cl.
CPC .................. *A61C 7/08* (2013.01); *A61C 7/12* (2013.01); *B33Y 70/00* (2014.12); *B33Y 80/00* (2014.12); *C08F 220/18* (2013.01); *C08F 220/28* (2013.01); *C08F 220/68* (2013.01); *C08F 222/10* (2013.01); *C08F 222/1006* (2013.01); *C08F 226/08* (2013.01); *C08G 75/26* (2013.01);

(Continued)

(58) Field of Classification Search
CPC ........................................................ A61C 7/08
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

International Search Report and Written Opinion for International Application No. PCT/IB2016000970, Search completed Sep. 28, 2016, dated Oct. 5, 2016, 10 Pgs.

(Continued)

*Primary Examiner* — Larry W Thrower
(74) *Attorney, Agent, or Firm* — Wilson Sonsini Goodrich & Rosati

(57) ABSTRACT

Provided herein are crosslinked polymers useful in orthodontic appliances and light polymerizable liquid compositions and formulations useful for making crosslinked polymers. Also provided are methods of making an orthodontic appliance comprising a cross-linked polymer formed by a direct fabrication technique.

14 Claims, 2 Drawing Sheets

(51) Int. Cl.
  *C08F 220/68* (2006.01)
  *C08F 226/08* (2006.01)
  *C08G 75/26* (2006.01)
  *B33Y 80/00* (2015.01)
  *B33Y 70/00* (2015.01)

(52) U.S. Cl.
  CPC ............... *C08F 2222/1086* (2013.01); *C08F 2222/1093* (2013.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |

(56) References Cited

U.S. PATENT DOCUMENTS

| | | | |
|---|---|---|---|
| 6,482,298 | B1 | 11/2002 | Bhatnagar |
| 6,524,101 | B1 | 2/2003 | Phan et al. |
| 6,554,611 | B2 | 4/2003 | Shishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 6,749,414 | B1 | 6/2004 | Hanson et al. |
| 7,641,828 | B2 | 1/2010 | DeSimone et al. |
| 7,892,474 | B2 | 2/2011 | Shkolnik et al. |
| 8,703,026 | B2 | 4/2014 | DeSimone et al. |
| 8,758,009 | B2 | 6/2014 | Chen et al. |
| 8,765,031 | B2 | 7/2014 | Li et al. |
| 8,807,999 | B2 | 8/2014 | Kuo et al. |
| 2002/0006597 | A1 | 1/2002 | Andreiko et al. |
| 2003/0003172 | A1 | 1/2003 | Stange et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2006/0078688 | A1* | 4/2006 | DeSimone ............... A61C 7/08 427/496 |
| 2006/0078841 | A1 | 4/2006 | DeSimone et al. |
| 2009/0246724 | A1 | 10/2009 | Chen et al. |
| 2012/0231232 | A1 | 9/2012 | Xu et al. |
| 2013/0302742 | A1 | 11/2013 | Li et al. |
| 2014/0061974 | A1 | 3/2014 | Tyler et al. |
| 2014/0265034 | A1 | 9/2014 | Dudley et al. |
| 2015/0004553 | A1 | 1/2015 | Li et al. |
| 2015/0097315 | A1 | 4/2015 | DeSimone et al. |
| 2015/0097316 | A1 | 4/2015 | DeSimone et al. |
| 2015/0102532 | A1 | 4/2015 | DeSimone et al. |
| 2015/0159059 | A1 | 6/2015 | Zhang et al. |
| 2017/0007359 | A1 | 1/2017 | Kopelman et al. |
| 2017/0007360 | A1 | 1/2017 | Kopelman et al. |
| 2017/0007361 | A1 | 1/2017 | Boronkay et al. |
| 2017/0007363 | A1 | 1/2017 | Boronkay |
| 2017/0007365 | A1 | 1/2017 | Kopelman et al. |
| 2017/0007366 | A1 | 1/2017 | Kopelman et al. |
| 2017/0007367 | A1 | 1/2017 | Li et al. |
| 2017/0007368 | A1 | 1/2017 | Boronkay |
| 2017/0007386 | A1 | 1/2017 | Mason et al. |
| 2017/0008333 | A1 | 1/2017 | Mason et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO 2017/007962 | 1/2017 |
| WO | WO 2017/007964 | 1/2017 |

OTHER PUBLICATIONS

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979- Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

(56) References Cited

OTHER PUBLICATIONS

Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, "Part 3 The Computer Gives New Vision—Literally," Part 4 Bytes 'N Bites—The Computer Moves from the Front Desk to the Operatory ,Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.

(56) References Cited

OTHER PUBLICATIONS

Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information—Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue ... The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue ... The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).
The Choice is Clear: Red, White & Blue ... The Simple, Affordable, No-Braces Treatment, Allesee Orthodontic Appliances—Pro Lab product information, 6 pages. (2003).

(56) References Cited

OTHER PUBLICATIONS

The Red, White & Blue Way to Improve Your Smile!Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pp. (2002).
European examination report dated Nov. 8, 2018 for EP Application No. 16739543.
European Intention to Grant dated Feb. 7, 2019 for EP Application No. 16739543.
Co-pending U.S. Appl. No. 16/432,596, filed Jun. 5, 2019.
Tumbleston et al. (Mar. 2015), "Continuous liquid interface production of 3D objects." *Science*, 347 (6228), 1349-1352.
Roylance (Oct. 2001), "Engineering Viscoelasticity," MIT Press. Cambridge, MA. 2001.
International Search Report and Written Opinion for International Application No. PCT/IB2016000970, Search completed Sep. 28, 2016, dated May 10, 2016, 10 Pgs.
U.S. Appl. No. 15/202,342, filed Jul. 5, 2016, 2017-0007361, Jan. 12, 2017.
U.S. Appl. No. 15/202,348, filed Jul. 5, 2016, 2017-0007368, Jan. 12, 2017.
U.S. Appl. No. 15/202,187, filed Jul. 5, 2016, 2017-0007359, Jan. 12, 2017.
U.S. Appl. No. 15/202,254, filed Jul. 5, 2016, 2017-0007360, Jan. 12, 2017.
U.S. Appl. No. 15/202,299, filed Jul. 5, 2016, 2017-0007363, Jan. 12, 2017.
U.S. Appl. No. 15/202,452, filed Jul. 5, 2016, 2017-0007366, Jan. 12, 2017.
U.S. Appl. No. 15/202,467, filed Jul. 5, 2016, 2017-0007367, Jan. 12, 2017.
U.S. Appl. No. 15/202,467, filed Jul. 5, 2016, 2017-0007367, Jan. 12, 21017.
U.S. Appl. No. 15/202,083, filed Jul. 5, 2016, 2017-0008333, Jan. 12, 2017.
U.S. Appl. No. 15/202,139, filed Jul. 5, 2016, 2017-0007386, Jan. 12, 3017.

* cited by examiner

DENTAL MATERIALS USING THERMOSET POLYMERS

CROSS-REFERENCE TO RELATED APPLICATIONS

This application claims the benefit of U.S. Provisional Application No. 62/189,380, filed Jul. 7, 2015 which is hereby incorporated by reference in its entirety.

BACKGROUND

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner. The appliance is configured to exert force on one or more teeth in order to effect desired tooth movements. The application of force can be periodically adjusted by the practitioner (e.g., by altering the appliance or using different types of appliances) in order to incrementally reposition the teeth to a desired arrangement.

FIG. 1A illustrates an exemplary orthodontic appliance 106 and jaw 104 including a patient's teeth, as presented in US Patent Application Publication 2015/0004553, the disclosure of which is incorporated herein by reference in its entirety. FIG. 1B illustrates orthodontic appliance cross-section 112 as taken along line 1B-1B of FIG. 1A, while FIG. 10 illustrates orthodontic appliance cross-section 118 as taken along line 1C-1C of FIG. 1A. The orthodontic appliance 106 may be designed to fit over a number of teeth present in an upper or lower jaw. As illustrated, the orthodontic appliance has a U-shaped cross-section to form one or more cavities for placement of a patient's teeth therein.

BRIEF SUMMARY

Provided herein are crosslinked polymers useful in orthodontic appliances and light polymerizable liquid compositions and formulations useful for making crosslinked polymers. Also provided are methods of making an orthodontic appliance comprising a cross-linked polymer formed by a direct fabrication technique. Direct fabrication can provide various advantages compared to other manufacturing approaches. For instance, in contrast to indirect fabrication, direct fabrication permits production of an appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness.

In many embodiments, direct fabrication is used to produce appliance geometries that would be difficult to create using alternative manufacturing techniques, such as appliances with very small or fine features, complex geometric shapes, undercuts, interproximal structures, shells with variable thicknesses, or internal structures (e.g., for improving strength with reduced weight and material usage). For instance, in many embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm. The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

Orthodontic appliances using the materials and method described herein include, but are not limited to, braces, retainers and shell aligners. The appliances can have different materials/formulation, shapes, and/or size/thickness from one area to another area with different force design in mind using multiple materials formulations. In embodiments, a multi-material direct fabrication method can involve forming an object from multiple materials in a plurality of sequential manufacturing steps. For instance, a first portion of the object (e.g., an interior layer) can be formed from a first material in accordance with any of the direct fabrication methods described herein, then a second portion of the object (e.g., an exterior layer) can be formed from a second material in accordance with methods herein, and so on, until the entirety of the object has been formed. In further embodiments, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety.

In embodiments, the orthodontic appliance is a tooth position adjustment dental appliance having cavities shaped to receive and resiliently reposition teeth from a first arrangement to a second arrangement. For example, a dental appliance can include a shell formed of cross-linked polymer materials and having a number of cavities to receive one or more teeth. In some embodiments, the shell is formed of thermoset polymer materials. In one or more apparatus embodiments, the dental appliance is an aligner (e.g., shell) having a number of cavities to receive one or more teeth. In embodiments, the aligner is one of a series of aligners corresponding to intermediate steps of an orthodontic treatment where the number of cavities are arranged to reposition the one or more teeth from a first configuration to a successive configuration, and the aligner is fabricated from material that is irreversibly cured to irreversibly link molecules into a rigid three dimensional structure. A dental appliance (e.g., a dental positioning appliance such as an aligner, a tray for delivery of chemicals in proximity to the teeth or gums, etc.) can include a number of cavities for receiving one or more corresponding teeth. In various embodiments, the cavities can correspond to one, or multiple, teeth, implants, and/or other features of a patient's jaw.

In embodiments, the crosslinked polymer comprises crosslinks formed by covalent interactions. In further embodiments, the crosslinked polymer also comprises crosslinks formed by non-covalent interactions. In embodiments, the crosslinked polymer is a thermoset polymer. In embodiments, the crosslinked polymer forms a crosslinked network.

In embodiments, the crosslinked polymer is selected from the group consisting of polyurethanes, (meth)acrylates, epoxies and copolymers thereof. As used herein, (meth) acrylate is shorthand for acrylate and/or methacrylate and a polyurethane polymer or oligomer includes at least one urethane linkage, also known as a carbamate linkage. In a further embodiment, the crosslinked polymer is an epoxy acrylate, a modified epoxy acrylate, epoxy methacrylate or a urethane acrylate. In embodiments, the crosslinked polymer is a copolymer. In embodiments, the crosslinked polymer is biocompatible. In different embodiments, the crosslinked polymer is transparent, translucent or opaque. Transparent crosslinked polymers may be clear or tinted to achieve various colors. In some embodiments the crosslinked polymer is characterized by a transmittance equal to or greater than 80% for light having a wavelength in the visible region.

In an aspect the crosslinked polymer has a tensile strength at yield of greater than 4000 psi (27.6 MPa) or from 20 MPa to 55 MPa. In embodiments, the tensile modulus is greater than 150,000 psi (1034 MPa) or from 800 MPa to 2000 MPa. In further embodiments, the elongation at yield is greater than 4%, greater than 4% and less than or equal to 25%, or greater than 4% and less than or equal to 10%. In additional embodiments, the elongation at break is greater than 30%, greater than 40%,greater than 40% and less than or equal to 250% or greater than 40% and less than or equal to 80%. Tensile and elongation properties may be measured per ASTM D 638-14. The water absorption may be less than one percent. In an embodiment, the glass transition temperature is greater than 90° C. and the deflection temperature is greater than 90° C. In further embodiments, the glass transition temperature is from 38° C. to 90° C. or from 40° C. to less than 90° C. In embodiments, the amount of stress relaxation at 37° C. at 24 hours and 100% relative humidity is such that the remaining load is greater than 80% of the initial load, greater than 50% of the initial load, greater than 25% of the initial load or greater than 10% of the initial load. In embodiments, the amount of stress relaxation at 37° C. at 14 days and 100% relative humidity is such that the remaining load is greater than 50% of the initial load, greater than 25% of the initial load or greater than 10% of the initial load. In further embodiments, the stress relaxation at 37° C. at 24 hours and 100% relative humidity is such that the remaining load is greater than 80% of the initial load (stress relaxation less than 20%) and at 14 days at 100% relative humidity the remaining load is greater than 50% of the initial load (stress relaxation less than 50%). In embodiments, the dimensional stability of the crosslinked polymer is such an orthodontic appliance including the crosslinked polymer meets dimensional specifications when placed in an oral environment, thereby maintaining fit of the appliance for the patient. In embodiments, the crosslinked polymer is used to form a shell of a tooth positioning aligner; the shell may span the entire arch.

In some aspects, a crosslinked polymer is provided having a tensile modulus, a tensile strength at yield, an elongation at yield and an elongation at break as described above. In some embodiments, a crosslinked polymer is provided having a tensile modulus from 800 MPa to 2000 MPa, a tensile strength at yield of 20 MPa to 55 MPa, an elongation at yield greater than 4% and an elongation at break greater than 30%.

In an aspect, the crosslinked polymers provided herein are formed by polymerization of a light polymerizable liquid composition or formulation comprising at least two polymerizable components. In a further aspect, the light polymerizable liquid composition comprises three polymerizable components. In embodiments, the light polymerizable liquid composition further comprises a photoinitiator. In further embodiments, the light polymerizable liquid composition further comprises a radical stabilizer, an inhibitor, a filler or a combination thereof. Suitable fillers include soluble filler and inorganic fillers.

In an aspect, a polymerizable component comprises at least one polymerizable group. Polymerizable groups include, but are not limited to, vinyl groups, ally groups, acrylate groups, methacrylate groups, acrylamide groups, epoxy groups and oxetanyl groups. As used herein, when a polymerizable component is stated to be a monomer or oligomer, a plurality of monomer or oligomer molecules of the specified type is intended to be included. A polymerizable component, such as a monomer or oligomer, may be characterized by the polymerizable groups of the monomer, by other functional groups of the monomer, or a combination thereof. As used herein, vinyl monomers or oligomers are monomers or oligomers including a vinyl group and include, but are not limited to, monomers or oligomers having acrylate, methacrylate or acrylamide groups. In some embodiments, vinyl monomers or oligomers not including meth (acrylate) groups are characterized as non-(meth) acrylate monomers or oligomers.

In embodiments, the formulation comprises at least one urethane (meth) acrylate prepolymer, monomer or oligomer. For example, the urethane (meth)acrylate prepolymer, monomer or oligomer is selected from the group consisting of Exothane 108, Exothane 10, isophorone urethane dimethacrylate (IPDI-UDMA), CN991, CN9782, CN3211, CN9782, CN9009, PU3201 NT and combinations thereof. In some embodiments, the urethane (meth)acrylate prepolymer, monomer or oligomer is an aliphatic urethane dimethacrylate. In other embodiments, the (meth)acrylate prepolymer, monomer or oligomer is an aliphatic urethane diacrylate. In further embodiments, the urethane (meth) acrylate prepolymer or oligomer has a viscosity of from 100,000 centipoise (cP) to 1,000,000 cP as measured at 25° C., from 10,000 cP to 50,000 cP as measured at 60° C., from 10,000 centipoise (cP) to 50,000 cP as measured at 25° C. or from 500 cP to 50,000 cP as measured at 60° C.

In additional embodiments, the formulation further comprises at least one vinyl monomer. For example, suitable vinyl monomers are selected from the group consisting of SR833S, SR368D, β-carboxyethylacrylate (CEA), and 1-vinyl-2-pyrrolidinone (NVP), M1130 (trimethyl cyclohexyl acrylate TMCHA), M151 (tetrahydrofurfuryl methacrylate, THFMA), isobornyl acrylate (IBOA), isobornyl methacrylate (IBOMA) and combinations thereof. In a further embodiment, the vinyl monomer is 1,3,5-Triallyl-1,3,5-triazine-2,4,6(1H,3H,5H)-trione (TATATO). TATATO may be used in combination with a thiol monomer. Exothane 108, Exothane 10, IPDI-UDMA or UDMA-IPDI (Esstech, Inc., identified as Isophorone Urethane dimethacrylate) are available from Esstech, Inc. (Essington, Pa.). CN991, CN9782 and CN3211, SR833S (also identified as 833 S, Tricyclodecane dimethanol diacrylate), SR368D (also identified as SR 368 D, Tris (2-hydroxy ethyl) isocyanurate triacrylate), CN9782, CN9009 and CN3211 are available from Sartomer (Exton, Pa.). PU3201NT, M1130, M151, IBOA, and IBOMA are available from Miwon (Anyang, South Korea). See also Table 3.

In embodiments, the vinyl monomer is a (meth)acrylate monomer which does not include a urethane linkage. Exemplary (meth)acrylate monomers which do not include a urethane linkage have a viscosity from 1 to 400 cP at 25° C. In embodiments, the number of (meth)acrylate functional groups is from 1 to 3.

In additional embodiments, the vinyl monomer does not include a urethane linkage or (meth)acrylate functional groups. Exemplary vinyl monomers which do not include a urethane linkage or (meth)acrylate functional groups include vinyl functional groups or allyl functional groups. In embodiments, such vinyl monomers have a viscosity from 1 to 200 cP at 25° C. In embodiment, the number of vinyl or allyl functional groups is from 1 to 3.

In a further aspect the formulation includes two polymerizable components. In some embodiments, the crosslinked polymer comprises a first repeating unit derived from a urethane (meth)acrylate oligomer and a second repeating unit derived from a vinyl or thiol monomer wherein at least one of the urethane (meth)acrylate oligomer, the vinyl monomer and the thiol monomer comprises at least two polymerizable groups. In an embodiment, amount of the first component is from 15-40 wt % and the amount of the second component is from 15 to 75 wt %.

In some embodiments, the crosslinked polymer comprises a first repeating unit derived from a urethane (meth)acrylate oligomer and a second repeating unit derived from a vinyl or thiol monomer wherein at least one of the urethane (meth)acrylate oligomer, the vinyl monomer and the thiol monomer comprises at least two polymerizable groups. The urethane (meth)acrylate oligomer and the vinyl or thiol monomer are as described herein. In some embodiments, the amount of the first repeating unit is from 25 to 50 wt % and the amount of the second repeating unit is from 50 to 75 wt %, with the total amount of the first repeating unit and the second repeating unit being greater than or equal to 70 wt %.

In an aspect, the formulations contain three polymerizable components. The first component may be regarded as a base component. In embodiments, the first component is a monomer or oligomer. In embodiments the first component is selected from the group of consisting of acrylates, methacrylates, vinyl esters, polyurethane with acrylate end groups and polyurethane with epoxy end groups. As examples, the first component comprises a functional group selected from polyurethane, acrylate, methacrylate, vinyl ester, epoxy, oxetanyl and combinations thereof. In further embodiments, the first component comprises a functional group selected from polyurethane, acrylate, epoxy, and combinations thereof. Some biocompatible monomers include tetraethylene glycol diacrylate (E4-A), diisopropyl acrylamide (DPA), diisobutylacrylamide (DBA), 2-(2-ethoxy-ethoxy) ethyl acrylate, trimethylolpropanetriacrylate (TTA) and urethanedimethacrylate (UDMA).

In embodiments, the first component is a urethane (meth)acrylate monomer or oligomer. In embodiments the urethane portion of the monomer or oligomer may be aliphatic or aromatic. In embodiments, the number of (meth)acrylate groups in the monomer is 1, 2 or 3. In further embodiments, the urethane (meth)acrylate monomer or oligomer is selected from the group consisting of a dimethacrylate urethane oligomer, an isophorone urethane dimethacrylate oligomer, a urethane diacrylate oligomer and a urethane triacrylate oligomer. As examples, suitable urethane (meth) acrylate monomers and oligomers are selected from the group consisting of Exothane 108, Exothane 10, IPDI-UDMA, CN991, CN9782, CN9782, CN3211, CN9009, PU3201NT and combinations thereof. In embodiments, the first component is selected from the group consisting of Exothane 108, Exothane 10, IPDI-UDMA or UDMA-IPDI (identified as Isophorone Urethane dimethacrylate), CN991, CN9782, CN9009, PU3201NT and CN3211. In some embodiments, the viscosity of the first component is greater than the viscosity of the other monomer or oligomer components in the formulation.

In some embodiments, the second component may be regarded as a reactive diluent. In embodiments, the second component comprises a functional group selected from polyurethane, acrylate, methacrylate, vinyl ester, epoxy, and combinations thereof. As examples, the second component is an acrylate, epoxy or urethane based diluent. In some embodiments, the second component is a vinyl monomer or a thiol monomer. As examples, the second component is selected from the group consisting of diacrylate monomers, triacrylate monomers, acyclic diacrylate monomers, cyclic diacrylate monomers, methacrylate monomers, vinyl ester monomers, polyurethane monomers with acrylate end groups and polyurethane monomers with epoxy end groups. In further embodiments, the third component is a vinyl monomer which does not include a urethane group. Such vinyl monomers include (meth)acrylate monomers and vinyl monomers which do not include (meth)acrylate groups. As examples, the second component is selected from 1-vinyl-2-pyrrolidinone (NVP), CEA β-carboxyethylacrylate), trimethyl cyclohexyl acrylate (M1130), isobornyl acrylate (IBOA), Isobornyl methacrylate (IBOMA), tetrahydrofurfuryl methacrylate (M151) and one of PETMP and TATATO (see Table 4). In some embodiments, the viscosity of the reactive diluent component(s) (e.g. the second component) is less than the viscosity of other monomer or oligomer components in the formulation (e.g. the first and the third components).

In some embodiments, the third component may be regarded as a modifier. In embodiments, the third component is a vinyl monomer or a thiol monomer. In further embodiments, the third component is a urethane (meth)acrylate monomer or oligomer. In embodiments the urethane portion of the monomer or oligomer may be aliphatic or aromatic. In an embodiment, the number of (meth)acrylate groups in the monomer is 1 or 2. In further embodiments, the third component is a vinyl monomer which does not include a urethane group. Such monomers include (meth)acrylate monomers. In an embodiment in which the formulation includes a thiol-ene system, the second component is one of a vinyl monomer or a thiol and the third component is the other of a vinyl monomer or a thiol. For example, when the second component is one of PETMP and TATATO, the third component is the other of PETMP and TATATO. As examples, the third component is selected from SR833S, SR368D, CN9782, CN3211, tris(2-hydroxy ethyl)isocyanurate triacrylate (M370), tricyclodecane dimethanol diacrylate (TCDDA), PE210, tripropylene glycol diacrylate (TPGDA), PU340, ME2110 and NVP (see Tables 3 and 4). In some embodiments, the viscosity of the modifier component(s) (e.g. the second component) is less than the viscosity of the first component in the formulation.

In embodiments of a formulation including three polymerizable components, the amount of the first repeating unit is from 15-40 wt %, the amount of the second repeating unit is from 15 to 75 wt % and the amount of the third repeating unit is from 2 to 60 wt %. In a further embodiment, the total amount of the first repeating unit, the second repeating unit and the third repeating unit is greater than or equal to 70 wt %. 80 wt % or 90 wt %. In further embodiments the amount of the first repeating unit is from 20-35 wt %, the amount of the second repeating unit is from 20 to 70 wt % and the amount of the third repeating unit is from 2 to 45 wt %, 2 to 20 wt %, 15 to 45 wt % or 20 to 40 wt %. In yet a further embodiment, the total amount of the first repeating unit, the second repeating unit and the third repeating unit being greater than or equal to 70 wt %. 80 wt % or 90 wt %.

An exemplary formulation comprising three polymerizable components includes a urethane (meth)acrylate monomer or oligomer and two vinyl monomers, each of which does not include a urethane group. In some embodiments, one of the vinyl monomers is an acrylate monomer. An exemplary formulation includes a urethane (meth) acrylate prepolymer, a non-urethane acrylate monomer and a non-acrylate vinyl monomer. Another exemplary formulation includes a urethane (meth)acrylate prepolymer and two non-urethane acrylate monomers. Another exemplary formulation with three polymerizable components includes two different urethane (methacrylate) monomers or oligomers and a vinyl monomer which does not include a urethane group. Another exemplary formulation with three polymerizable components includes two different urethane (methacrylate) monomers or oligomers and a vinyl monomer which does not include a urethane group or an acrylate group. A further exemplary formulation includes a urethane (methacrylate) monomer or oligomer, a thiol monomer and a vinyl monomer, wherein neither the thiol monomer nor the vinyl monomer includes a urethane group.

In an aspect, the crosslinked polymer comprises a first repeating unit derived from a first urethane (meth) acrylate oligomer, a second repeating unit derived from a first vinyl or thiol monomer not including a urethane linkage and a third repeating unit derived from a second urethane (meth) acrylate oligomer or a second vinyl or thiol monomer not including a urethane linkage, wherein at least one of the urethane (meth) acrylate oligomer(s) and the vinyl or thiol monomer(s) comprises at least two polymerizable groups. In some embodiments, the amount of the first repeating unit is from 15-40 wt %, the amount of the second repeating unit is from 15 to 75 wt % and the amount of the third repeating unit is from 2-60 wt %, with the total amount of the first repeating unit, the second repeating unit and the third repeating unit being greater than or equal to 70 wt %.

Photoinitiators suitable for use in the polymerizable liquid compositions of the invention include, but are not limited to photoinitiators activated by UV or visible light. In embodiments, the photoinitiator is activated by long-wavelength UV light or UVA (wavelength approximately 320 to 400 nm). Photo-initiators activated by long wavelength UV light include, but are not limited to, 2, 4, 6-trimethylbenzoylphenyl phosphinate (Irgacure®TPO-L), acylgermanes, a bimolecular system of camphorquinone (CQ) and N, N-dimethylaminobenzoic acid ethyl ester (DMAB), bisacylphosphine oxides (Irgacure 819) and hydroxyalkylphenones (Irgacure 2959) and 1,5-diphenyl-1,4-diyn-3-one (Diinone). Camphorquinone (CQ), N, N-dimethylaminobenzoic acid ethyl ester (DMAB) bisacylphosphine oxides (Irgacure 819), hydroxyalkylphenones (Irgacure 2959) and 1,5-diphenyl-1, 4-diyn-3-one (Diinone) are biocompatible. In some embodiments, the formulation includes from 0.1 wt % to 3 wt % photoinitiator. In further embodiments, the formulation does not include a second type of initiator other than a photoinitiator.

In an aspect, the viscosity of the polymerizable liquid composition is suitable for use with a direct or additive manufacturing process. In embodiments, the viscosity of the polymerizable liquid composition is less than 4000 cP, less than 2000 cP, less than 700 cP, from greater than or equal to 500 cP to less than 4000 cP, from greater than or equal to 500 cP to less than 2000 cP, from greater than or equal to 200 cP to less than 4000 cP or from greater than or equal to 200 cP to less than 2000 cP. The viscosity may be measured at the process temperature. The process temperature can be adjustable from room temperature (~25° C.) to higher temperature such as 80° C. or higher in order to achieve the desired process viscosity and speed.

In an aspect, the crosslinked polymer is formed via a direct or additive manufacturing process. Direct or additive manufacturing processes may also be termed 3D printing. Suitable manufacturing processes include, but are not limited to, stereolithography (SLA), micro-stereolithography (μSLA), DLP projection, 2PP (two photon polymerization), continuous liquid interface production and material jetting. In embodiments, the direct fabrication methods described herein build up the object geometry in a layer-by-layer fashion, with successive layers being formed in discrete build steps. In particular embodiments, an at least partially crosslinked polymer is formed by sequential formation of polymer layers on a surface of a build plate, wherein at least that surface of the build plate is immersed in a vat or reservoir of a formulation comprising polymerizable components. In embodiments the polymer is formed by exposure of the formulation to light of suitable wavelengths and intensity to activate the photoinitiator in the formulation and cause photopolymerization of polymerizable components in the formulation. The build plate is typically moved with respect to the vat or reservoir (e.g., along the vertical or Z-direction) during the irradiation phase. In some embodiments, the build plate is moved away from the free surface of the formulation (e.g. moved deeper into the vat) as irradiation progresses. In other embodiments, the build plate is moved away from the base of the vat as irradiation progresses.

Alternatively or in combination, direct fabrication methods that allow for continuous or nearly continuous build-up of an object geometry can be used, referred to herein as "continuous direct fabrication." Various types of continuous direct fabrication methods can be used. As an example, in embodiments, the crosslinked polymers herein are fabricated using "continuous liquid interphase printing," in which an object is continuously built up from a reservoir of photopolymerizable resin by forming a gradient of partially cured resin between the building surface of the object and a polymerization-inhibited "dead zone." In many embodiments, a semi-permeable membrane is used to control transport of a photopolymerization inhibitor (e.g., oxygen) into the dead zone in order to form the polymerization gradient. In an embodiment, the oxygen concentration is greater near the base of the reservoir than at the surface of the build plate and the build plate is moved away from the base of the reservoir during irradiation. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

The crosslinked polymer may undergo post processing following direct fabrication. In some embodiments, the crosslinked polymer may be subjected to chemical extraction to remove small molecule contents (e.g. uncured or unpolymerized monomers and/or oligomers, photoinitiators and other components). In embodiments, a single solution or multiple solutions are used for chemical extraction. As an example, multiple solutions used for extraction differ in the nature and/or concentration of the solution components. The processes can also include a dual curing system in order to achieve a high level of curing of the final parts. In embodiments, an initial level of crosslinking is achieved during the deposition of the part and a further crosslinking is achieved by additional exposure to light ("post-curing"). In a further embodiment, the first step is to be achieved with slower reaction with mixing catalysts or fast reaction by light source: the second step will be completed with a gamma source e-beam, or heat for a continuous process. In embodiments, the light source provides UV light.

In some embodiments, methods of making an orthodontic appliance comprising a cross-linked polymer comprise the steps of:

providing a light polymerizable liquid composition comprising:

a first polymerizable component, wherein the first polymerizable component is selected from the group consisting of an acrylate monomer or oligomer, a methacrylate monomer or oligomer, a vinyl ester monomer or oligomer, an acrylamide monomer or oligomer; a thiol monomer or oligomer, urethane monomer or oligomer, an epoxy monomer or oligomer and a oxetane monomer or oligomer;

a second polymerizable component, wherein the second polymerizable component is a vinyl monomer or oligomer, thiol monomer or oligomer, a urethane monomer or oligomer and an epoxy monomer or oligomer; and a photoinitiator;

wherein at least one of the first and second polymerizable components comprises at least two polymerizable groups; and fabricating the cross-linked polymer by a direct fabrication technique.

The liquid polymerizable liquid compositions or formulations are as described elsewhere herein. Similarly, suitable fabrication techniques are described herein.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding.

For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

BRIEF DESCRIPTION OF THE DRAWINGS

FIG. 1B illustrates dental appliance cross-section 112 as taken along line 1B-1B of FIG. 1A, while FIG. 10 illustrates dental appliance cross-section 118 as taken along line 1C-1C of FIG. 1A.

DETAILED DESCRIPTION

Figure 1A:
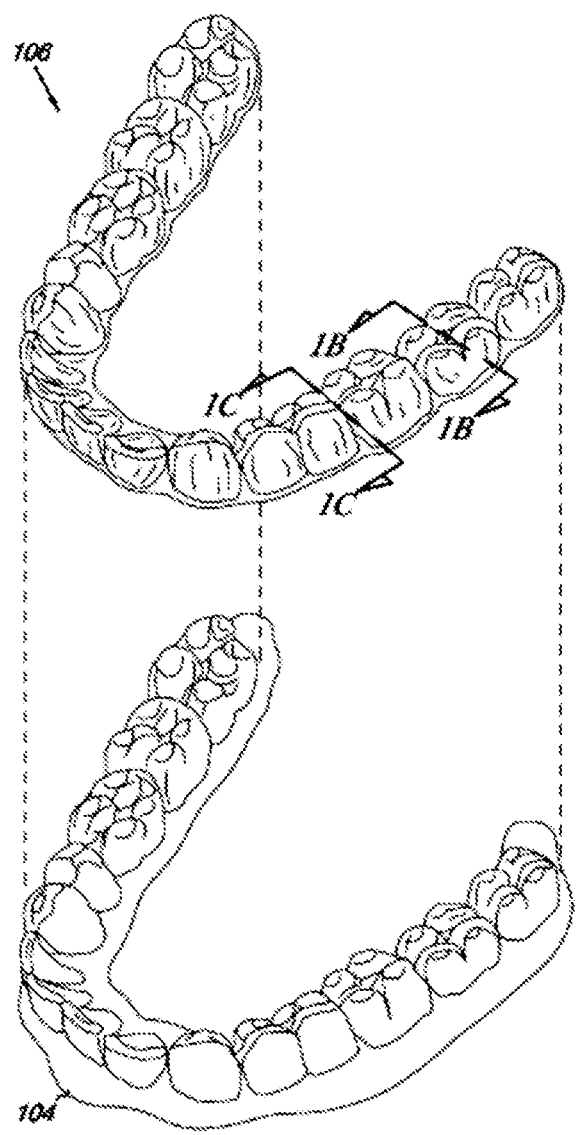
FIG. 1A illustrates an exemplary dental appliance 106 and jaw 104 including a patient's teeth.
Figure 1B:
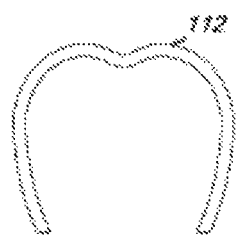
Figure 1C:
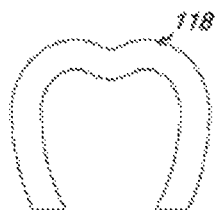

As used herein, the term "polymer" refers to a molecule composed of repeating structural units connected by covalent chemical bonds often characterized by a substantial number of repeating units (e.g., equal to or greater than 10 repeating units and often equal to or greater than 50 repeating units and often equal to or greater than 100 repeating units) and a high molecular weight (e.g. greater than or equal to 50,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, alternating, segmented, grafted, tapered and other copolymers.

An "oligomer" refers to a molecule composed of repeating structural units connected by covalent chemical bonds often characterized by a number of repeating units less than that of a polymer (e.g., equal to or less than 10 repeating units) and a lower molecular weights (e.g. less than or equal to 50,000 Da) than polymers. Oligomers may be the polymerization product of one or more monomer precursors. In an embodiment, an oligomer or a monomer cannot be considered a polymer in its own right.

A "prepolymer" refers to a polymer or oligomer the molecules of which are capable of entering, through reactive groups, into further polymerization. Routes to forming polyurethane polymers include polymerization of diol and diisocyanate monomers and polymerization of prepolymers including urethane linkages. In embodiments, the polyurethane prepolymer is oligomeric. In father embodiments, the polyurethane prepolymers include acrylate or methacrylate endgroups.

Oligomers and polymer mixtures can be characterized and differentiated from other mixtures of oligomers and polymers by measurements of molecular weight and molecular weight distributions. The following definitions of molecular weight can be applied for such characterization (see: L. H. Sperling, Introduction to Physical Polymer Science, $2^{nd}$ Ed., Wiley New York (1992).) The average Molecular Weight (M) is the Average Number of Repeating Units n (or dp.)×the molecular weight or molar mass (Mi) of the repeating unit. The number-average molecular weight ($M_n$) is the arithmetic mean, representing the total weight of the molecules present divided by the total number of molecules. Molecular weight may also be measured by the weight-average molecular weight (Mw) and the z-average molecular weight Mz, In embodiments, one or more monomers or oligomers in the light polymerizable liquid composition contains one or more vinyl functional groups, which contain one or more carbon-carbon double bonds. The vinyl functional groups in the system may be provided by, for example, allyl ethers, vinyl ethers, norbornenes, acrylates, methacrylates, acrylamides or other monomers containing vinyl groups. In embodiments, the vinyl monomer or oligomer has at least one vinyl functional group, at least two vinyl functional groups, at least three vinyl functional groups or at least four vinyl functional groups or from 2 to 4 thiol functional groups. In some embodiments, the vinyl monomer or oligomer may further comprise a hydroxyl group. In other embodiments, the vinyl monomer or oligomer does not comprise a hydroxyl group.

In embodiments, one of the monomers or oligomers in the light polymerizable liquid composition includes a thiol monomer or oligomer. As used herein, a thiol monomer or oligomer containing one or more thiol functional groups, which terminate with —SH. Monomers or oligomers containing thiol functional groups may be combined with monomers or oligomers comprising at least one aliphatic carbon-carbon double bond or at least one aliphatic carbon-carbon triple bond. In embodiments, the thiol monomer or oligomer has at least two thiol functional groups, at least three thiol functional groups or at least four thiol functional groups or from 2 to 4 thiol functional groups. In different embodiments, a thiol-ene system has about 1-90% of its functional groups as thiol functional groups or 2%-65% thiol functional groups. The balance of the functional groups (35% to 98%) of the functional groups may be vinyl functional groups.

In embodiments, the light polymerizable composition further includes a filler material. Soluble filler materials include, but are not limited to poly(vinyl alcohol), poly (vinyl butyral-co-vinyl alcohol-co-vinyl acetate), polycaprolactone, poly (methyl methacrylate), polycaprolactone-block-polytetrahydrofuran block-polycaprolactone, poly (vinyl chloride) or cellulose acetate butyrate, which may be used to tune the viscosity. Inorganic fillers include, but are not limited to hydroxyapatite, fumed silica, colloidal silica, glass powders and β-tricalciumphosphate, which may be used to improve the mechanical properties of the polymer.

Photoinitiators that are useful in the invention include those that can be activated with light and initiate polymerization of the polymerizable components of the formulation. In embodiments, the photoinitiator is a radical photoinitiator or a cationic initiator. In a further embodiment, the photoinitiator is a Type I photoinitiator which undergoes a unimolecular bond cleavage to generate free radicals. In an additional embodiment the photoinitiator is a Type II photoinitiator which undergoes a bimolecular reaction to generate free radicals. Common Type I photoinitiators include, but are not limited to benzoin ethers, benzil ketals, α-di-alkoxy-acetophenones, α-hydroxy-alkyl phenones and acylphosphine oxides. Common Type II photoinitiators include benzophenones/amines and thioxanthones/amines. Cationic initiators include aryldiazonium, diaryliodonium, and triarylsulfonium salts.

Photopolymerization occurs when suitable formulations are exposed to light of sufficient power and of a wavelength capable of initiating polymerization. The wavelengths and power of light useful to initiate polymerization depends on the initiator used. Light as used herein includes any wavelength and power capable of initiating polymerization. Preferred wavelengths of light include ultraviolet (UV) or visible. UV light sources include UVA (wavelength about 400 nm to about 320 nm), UVB (about 320 nm to about 290 nm) or UVC (about 290 nm to about 100 nm). Any suitable source may be used, including laser sources. The source may be broadband or narrowband, or a combination. The light source may provide continuous or pulsed light during the process. Both the length of time the system is exposed to UV light and the intensity of the UV light can be varied to determine the ideal reaction conditions.

Additive manufacturing includes a variety of technologies which fabricate three-dimensional objects directly from digital models through an additive process. In some aspects, successive layers of material are deposited and "cured in place." A variety of techniques are known to the art for additive manufacturing, including selective laser sintering (SLS), fused deposition modeling (FDM) and jetting or extrusion. In many embodiments, selective laser sintering involves using a laser beam to selectively melt and fuse a layer of powdered material according to a desired cross-sectional shape in order to build up the object geometry. In many embodiments, fused deposition modeling involves melting and selectively depositing a thin filament of thermoplastic polymer in a layer-by-layer manner in order to form an object. In yet another example, 3D printing can be used to fabricate the appliances herein. In many embodiments, 3D printing involves jetting or extruding one or more materials onto a build surface in order to form successive layers of the object geometry.

Photopolymers may be fabricated by "vat" processes in which light is used to selectively cure a vat or reservoir of the photopolymer. Each layer of photopolymer may be selectively exposed to light in a single exposure or by scanning a beam of light across the layer. Specific techniques include sterolithography (SLA), Digital Light Processing (DLP) and two photon-induced photopolymerization (TPIP).

Continuous direct fabrication methods for photopolymers have also been reported. For example, a direct fabrication process can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety. In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety. Continous liquid interface production of 3D objects has also been reported (J. Tumbleston et al., Science, 2015, 347 (6228), pp 1349-1352) hereby incorporated by reference in its entirety for description of the process. Another example of continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

"Biocompatible" refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a human or animal is exposed to or in contact with the biocompatible material. Alternatively, immune response may be determined histologically, wherein localized immune response is assessed by visually assessing markers, including immune cells or markers that are involved in the immune response pathway, in and adjacent to the material. In an aspect, a biocompatible material or device does not observably change immune response as determined histologically. In some embodiments, the invention provides biocompatible devices configured for long-term use, such as on the order of weeks to months, without invoking an adverse immune response. Biological effects may be initially evaluated by measurement of cytotoxicity, sensitization, irritation and intracutaneous reactivity, acute systemic toxicity, pyrogenicity, subacute/subchronic toxicity and/or implantation. Biological tests for supplemental evaluation include testing for chronic toxicity.

"Bioinert" refers to a material that does not elicit an immune response from a human or animal when it is disposed within an in-vivo biological environment. For example, a biological marker indicative of an immune response remains substantially constant (plus or minus 5% of a baseline value) when a human or animal is exposed to or in contact with the bioinert material. In some embodiments, the invention provides bioinert devices.

In embodiments, the crosslinked polymers are characterized by a tensile stress-strain curve that displays a yield point after which the test specimen continues to elongate, but there is no increase in load. Such yield point behavior typically occurs "near" the glass transition temperature, where the material is between the glassy and rubbery regimes and may be characterized as having viscoelastic behavior. In embodiments, viscoelastic behavior is observed in the temperature range 20° C. to 40° C. The yield stress is determined at the yield point. In some embodiments, the yield point follows an elastic region in which the slope of the stress-strain curve is constant or nearly constant. In embodiments, the modulus is determined from the initial slope of the stress-strain curve or as the secant modulus at 1% strain (e.g. when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by $\ln(I/I_0)$, which may be approximated by $(I-I_0)/I_0$ at small strains (e.g. less than approximately 10%) and the elongation is $I/I_0$, where I is the gauge length after some deformation has occurred and $I_0$ is the initial gauge length. The mechanical properties can depend on the temperature at which they are measured. The test temperature may be below the expected use temperature for a dental appliance such as 35° C. to 40° C., In embodiments, the test temperature is 23±2° C.

In embodiments, the stress relaxation can be measured by monitoring the time-dependent stress resulting from a steady strain. The extent of stress relaxation can also depend on the temperature. In embodiments, the test temperature is 37±2° C.

The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2/s$. Devices for measuring viscosity include viscometers and rheometers.

Examples of devices that may be made by direct fabrication include, but are not limited to, those described in the following U.S. Provisional Applications filed Jul. 7, 2015: "MULTI-MATERIAL ALIGNERS", U.S. Ser. No. 62/189,259; "DIRECT FABRICATION OF ALIGNERS WITH INTERPROXIMAL FORCE COUPLING", U.S. Ser. No. 62/189,263; "DIRECT FABRICATION OF ORTHODONTIC APPLIANCES WITH VARIABLE PROPERTIES", U.S. Ser. No. 62/189,291; "DIRECT FABRICATION OF ALIGNERS FOR ARCH EXPANSION", U.S. Ser. No. 62/189,271; "DIRECT FABRICATION OF ATTACHMENT TEMPLATES WITH ADHESIVE", U.S. Ser. No. 62/189,282; "DIRECT FABRICATION CROSS-LINKING FOR PALATE EXPANSION AND OTHER APPLICATIONS", U.S. Ser. No. 62/189,301; "SYSTEMS, APPARATUSES AND METHODS FOR DENTAL APPLIANCES WITH INTEGRALLY FORMED FEATURES", U.S. Ser. No. 62/189,312; "DIRECT FABRICATION OF POWER ARMS", U.S. Ser. No. 62/189,317; "SYSTEMS, APPARATUSES AND METHODS FOR DRUG DELIVERY FROM DENTAL APPLIANCES WITH INTEGRALLY FORMED RESERVOIRS", U.S. Ser. No. 62/189,303 and "DENTAL APPLIANCE HAVING ORNAMENTAL DESIGN", U.S. Ser. No. 62/189,318, each of which is hereby incorporated by reference in its entirety.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

STATEMENTS REGARDING CHEMICAL COMPOUNDS AND NOMENCLATURE

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those that are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-member aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the invention at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the invention include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as attaching and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as attaching and/or spacer groups. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br) or iodo (—I)

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)n-alkoxy wherein n is an integer from 1 to 10, preferably 1 to 4, and more preferably for some embodiments 1 to 3.

As to any of the groups described herein that contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN, —OCN (cyanate), —NCO (isocyanate), —SCN (thiocyanate) and —NCS (isothiocyanate);

—COOR, where R is a hydrogen or an alkyl group or an aryl group and more specifically where R is a methyl, ethyl, propyl, butyl, or phenyl group all of which groups are optionally substituted;

—COR, where R is a hydrogen or an alkyl group or an aryl group and more specifically where R is a methyl, ethyl, propyl, butyl, or phenyl group all of which groups are optionally substituted;

—CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR, where R is an alkyl group or an aryl group and more specifically where R is a methyl, ethyl, propyl, butyl, or phenyl group, all of which are optionally substituted;

—OCOOR, where R is an alkyl group or an aryl group;

—SO$_2$N(R)$_2$, where each R, independently of each other R, is a hydrogen, or an alkyl group, or an aryl group all of which are optionally substituted and wherein R and R can form a ring that can contain one or more double bonds and can contain one or more additional carbon atoms;

—OR, where R is H, an alkyl group, an aryl group, or an acyl group all of which are optionally substituted. In a particular example R can be an acyl yielding —OCOR", wherein R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this invention include all stereochemical isomers arising from the substitution of these compounds.

The invention may be further understood by the following non-limiting examples.

EXAMPLE 1

Properties for Selected Formulations and Testing Methods

Table 1 gives exemplary formulations which were measured as having a modulus in the range 800 MPa to 2000 MPa, a tensile strength of 20 MPa to 55 mPa, an elongation at yield greater than 4% and a elongation@break greater than 40% (composition ratios by weight):

TABLE 1

| Formulation | Composition |
|---|---|
| Exo10/CEA/NVP | 30/50/20 |
| Exo10/PETMP:TATATO | 30/70 (2:1.1) |
| Exo10/CEA/NVP | 20/70/10 |
| CN3211/CEA/NVP | 20/60/20 |

Table 2 gives exemplary formulations which were measured as having a modulus in the range 800 MPa to 2000 MPa, a tensile strength of 20 MPa to 55 mPa, an elongation at yield greater than 4% and a elongation@break from 30% to 40% (composition ratios by weight):

TABLE 2

| Formulation | Composition |
|---|---|
| Exo108/NVP/CEA | 33/33/33 |
| Exo108/CEA/SR833S | 30/50/20 |
| CN991/NVP/CEA | 20/40/40 |
| CN991/NVP/CN9782 | 30/60/10 |
| Exo108/IBOA/NVP | 20/20/60 |
| CN3211/CEA/IPDI-UDMA | 20/60/20 |
| CN3211/CEA/SR833S | 20/60/20 |

Protocols

The mixing protocol was as follows. All of the formulations were mixed with a Flacktek Speedmixer™ (1.5 minutes at 2700 rpm) and contained 0.5 wt % TPO-L as the photoinitiator.

The curing protocol was as follows. The samples were cured into dog bone molds, 1 mm thickness, 6 mm width and 12 or 35 mm length. Samples were cured with a 395 nm LED light at an intensity of 10 mW/cm² for 45 seconds or with a 385 nm Heraeus NobleCure light at an intensity of 80 mW/cm² for 15 seconds.

The tensile properties protocol was as follows. Tensile properties were measured with a TestResources Materials Testing System. The crosshead speed was 2.5 mm/min. The dog bones were 35 mm long for assessment of mechanical properties for Tables 1 and 2.

TABLE 3

Acrylate Monomers and Oligomers

| Product Code | Chemical Name/Classification | Viscosity (cP) |
|---|---|---|
| SR 833S | Tricyclodecane dimethanol diacrylate | 130 @ 25 C. |
| SR 368D | Tris (2-hydroxy ethyl) isocyanurate triacrylate | 330 @ 25 C. |
| SR 368 | Tris (2-hydroxy ethyl) isocyanurate triacrylate | |
| CN 991 | Aliphatic urethane diacrylate oligomer | 600 @ 60 C. |
| CN 9782 | Aromatic urethane diacrylate oligomer | 42000 @ 60 C. |
| CN 3211 | Aliphatic urethane acrylate oligomer | 27500 @ 25 C. |
| CN 9009 | Urethane acrylate | |
| PU 3201NT | Aliphatic trifunctional methacrylate | 15,000 @ 25 C. |
| PE210 | Bisphenol A Epoxy Acrylate | 5,000 @ 60 C. |
| TPGDA | Tripropylene glycol diacrylate | 15-20 @ 25 C. |
| PU340 | Aliphatic trifunctional acrylate | 70,000 @ 25 C. |
| ME 2110 | Modified epoxy acrylate | 4,000 @ 65 C. |
| Exo10 | Dimethacrylate urethane | 816000 @ 25 C. |
| Exo 108 | Dimethacrylate urethane | 176000 @ 25 C. |
| IPDI-UDMA | Isophorone Urethane Dimethacrylate | |
| UDMA | Urethane dimethacrylate | |

TABLE 4

Additional Monomers

| Product Code | Chemical Name/Classification | Viscosity (cP) |
|---|---|---|
| IBOA | Isobornyl acrylate | 7 @ 25 C. |
| IBOMA | Isobornyl Methacrylate | |
| M1130 | Trimethyl cyclohexyl acrylate | 1-10 @ 25 C. |
| M151 | Tetrahydrofurfuryl methacrylate | 10 @ 25 C. |
| NVP | 1-vinyl-2-pyrrolidinone | 2 @ 20 C. |
| SR833S | Tricyclodecane dimethanol diacrylate | 130 @ 25 C. |
| TATATO | 1,3,5-Triallyl-1,3,5-triazine-2,4,6(1H,3H,5H)-trione | |
| PETMP | Pentaerythritol tetrakis(3-mercaptopropionate) | |
| CEA | β-carboxyethylacrylate | 73 @ 25 C. |

EXAMPLE 2

3D Printing

For 3D printing, samples were formulated with 0.1 or 0.08 wt % UV blocker (OB+, Mayzo, Suwanee, Ga.) and 2 or 0.5 wt % photoinitiator. An Auto Desk Ember 3D printer (DLP SLA) was utilized with a 405 nm LED projector and build plate with dimensions of 64 mm by 40 mm. The layer thickness was 25 μm and the exposure time was 4 seconds/layer. After printing, the parts were rinsed with methanol and post cured with the 385 nm Heraeus NobleCure light for 30 minutes.

We claim:

1. A crosslinked polymer for use in an orthodontic appliance, the crosslinked polymer comprising:
   a first repeating unit derived from a urethane (meth)acrylate oligomer;
   a second repeating unit derived from a vinyl or thiol monomer; and
   a tensile modulus from 800 MPa to 2000 MPa, a tensile strength at yield of 20 MPa to 55 MPa, an elongation at yield greater than 4% and an elongation at break greater than 30%.

2. The crosslinked polymer of claim 1, wherein at least one of the urethane (meth)acrylate oligomer, the vinyl monomer and the thiol monomer comprises at least two polymerizable groups.

3. The crosslinked polymer of claim 2, wherein the amount of the first repeating unit is from 25 to 50 wt % and the amount of the second repeating unit is from 50 to 75 wt %, with the total amount of the first repeating unit and the second repeating unit being greater than or equal to 70 wt %.

4. The crosslinked polymer of claim 1, wherein the crosslinked polymer further comprises a third repeating unit derived from a second urethane (meth)acrylate oligomer or a second vinyl or thiol monomer not including a urethane linkage, wherein at least one of the urethane (meth)acrylate oligomer(s) and the vinyl or thiol monomer(s) comprises at least two polymerizable groups.

5. The crosslinked polymer of claim 4, wherein the amount of the first repeating unit is from 15 to 40 wt %, the amount of the second repeating unit is from 15 to 75 wt % and the amount of the third repeating unit is from 2 to 60 wt %, with the total amount of the first repeating unit, the second repeating unit and the third repeating unit being greater than or equal to 70 wt %.

6. The crosslinked polymer of claim 4, wherein the second repeating unit is derived from a vinyl monomer not including a urethane linkage.

7. The crosslinked polymer of claim 4, wherein the second repeating unit is derived from 1-vinyl-2-pyrrolidinone (NVP), β-carboxyethylacrylate-(CEA), trimethyl cyclohexyl acrylate (TMCHA), tetrahydrofurfuryl methacrylate (THFMA), isobornyl acrylate (IBOA), or isobornyl methacrylate (IBOMA).

8. The crosslinked polymer of claim 1, wherein the urethane (meth)acrylate oligomer is selected from the group consisting of a urethane dimethacrylate oligomer, an isophorone urethane dimethacrylate oligomer, a urethane diacrylate oligomer, and a urethane triacrylate oligomer.

9. The crosslinked polymer of claim 1, wherein the second repeating unit is derived from an acrylate monomer.

10. The crosslinked polymer of claim 1, wherein the crosslinked polymer has a transmittance equal to or greater than 80% for light having a wavelength in the visible region.

11. The crosslinked polymer of claim 1, wherein the crosslinked polymer comprises a plurality of polymer layers.

12. The crosslinked polymer of claim 1, wherein the crosslinked polymer is transparent, translucent, or opaque.

13. The crosslinked polymer of claim 4, wherein the third repeating unit is derived from a urethane (meth)acrylate oligomer or vinyl monomer not including a urethane linkage.

14. The crosslinked polymer of claim 4, wherein the third repeating unit is derived from a thiol monomer.

* * * * *